United States Patent [19]
Mueller et al.

[11] Patent Number: 6,154,275
[45] Date of Patent: Nov. 28, 2000

[54] OPTICAL DISC INSPECTION EQUALIZATION SYSTEM AND METHOD

[75] Inventors: William R. Mueller, Clarks Summit; Lewis R. Gensel, Avoca; Peter Van Hoof, Moosic, all of Pa.

[73] Assignee: WEA Manufacturing Inc., Olyphant, Pa.

[21] Appl. No.: 09/316,632

[22] Filed: May 21, 1999

Related U.S. Application Data

[62] Division of application No. 08/920,299, Aug. 28, 1997, Pat. No. 5,940,174.
[60] Provisional application No. 60/028,861, Oct. 16, 1996.

[51] Int. Cl.[7] .................................................. G01N 21/00
[52] U.S. Cl. .................................. 356/237.1; 356/237.2; 250/201.5; 369/44.32
[58] Field of Search ........................... 356/237.1, 237.2, 356/244, 237.5, 445, 446, 371; 369/47, 58, 59; 360/128, 133; 250/562, 563

[56] References Cited

U.S. PATENT DOCUMENTS

| | | | |
|---|---|---|---|
| 4,069,484 | 1/1978 | Firester et al. | 356/237 |
| 4,197,011 | 4/1980 | Hudson | 356/237 |
| 4,508,450 | 4/1985 | Ohshima et al. | 356/237 |
| 4,699,268 | 10/1987 | Oishi | 360/128 |
| 4,794,264 | 12/1988 | Quackenbos et al. | 356/237.2 |
| 4,794,265 | 12/1988 | Quackenbos et al. | 250/572 |
| 4,954,723 | 9/1990 | Takahashi et al. | 356/237.2 |
| 5,031,112 | 7/1991 | Sakai et al. | 364/507 |
| 5,067,812 | 11/1991 | Sugimura et al. | 356/237 |
| 5,098,191 | 3/1992 | Noguchi et al. | 356/394 |
| 5,268,735 | 12/1993 | Hayashi | 356/237 |

FOREIGN PATENT DOCUMENTS 0 152 165 A2  8/1985  European Pat. Off. ....... G01N 21/88

OTHER PUBLICATIONS

Yoshizawai T. et al, "Measuring System For Optical Disk Mechanical Characteristics", *IEICE Transactions On Electronics*, E77–C: 1685–93, Oct. 1994.

Pietzsch K, "Laser–Scanner–System Zur Prüfung von Compact Discs", *Feinwerktechnik & Messtechnik*, 95:215–19, 1987.

Mather G.R., "Optical Disc Inspection By Linear Array CCD Systems", Proceeding Of The Midwest Symposium On Circuits And Systems, 2:1447–1455, Aug. 1993.

"Distinguishing Between Media Flaws And Contamination in Optical Drives" *IBM Technical Disclosure Bulletin*, 38:371–376, May 1995.

*Primary Examiner*—Hoa Q. Pham
*Attorney, Agent, or Firm*—Fish & Neave; Joseph M. Guiliano; Brajesh Mohan

[57] ABSTRACT

A system and method are provided that allow an optical media inspection device to detect defects on or in optical media despite the presence of gross deformations in the media that would otherwise interfere with the inspection process. A holding device holds the optical media near the center while it is rotated for inspection. A negative displacement prohibitor impedes any negative displacement of the optical media. A positive displacement inhibitor, i.e., air pressure exerted on the optical media, holds the optical media substantially flat while it is being inspected. A closed-loop feedback system may be used to control the amount of air pressure exerted against the optical media.

21 Claims, 6 Drawing Sheets

OPTICAL DISC INSPECTION EQUALIZATION SYSTEM AND METHOD

This is a division, of application Ser. No. 08/920,299, filed Aug. 28, 1997 now U.S. Pat. No. 5,940,174.

This claims the benefit of U.S. Provisional Application Ser. No. 60/028,861, filed Oct. 16, 1996.

BACKGROUND OF THE INVENTION

This invention relates to the inspection of optical media such as digital versatile discs ("DVDs"), compact discs ("CDs"), compact disc read-only memories ("CD ROMs"), and the like, via an inspection device, e.g., CCD camera (cameras that typically include an array of charge-coupled devices to capture the image), laser diode, or any other similar inspection device. More particularly, this invention relates to a system and method that allows an optical media inspection device to accurately detect defects on or in the optical media despite the presence of gross deformations (e.g., warping or bending) in the optical media which may interfere with the detection of the defects being sought.

It is important in the manufacturing of optical media to check for anomalies that may compromise the quality of performance of the optical media. Defects on the surface, or in one or more of the layers of the optical media, may lead to data errors that cannot be corrected by the device (e.g., CD player, DVD player or computer) used to read the optical media. Moreover, a defect caused by a manufacturing problem may appear in thousands of copies of the media. Detection of such defects gives the manufacturers the opportunity to withhold the release of defective media to consumers and to correct manufacturing problems that may be causing the defects.

Inspection of optical media using a CCD camera, laser diode, or other similar inspection devices is well known. Commercially available inspection devices include, for example, iNSPECT® of Medar Inc. of Farmington Hills, Mich. and S2® of Basler of Malvern, Pa. Often, these devices work by measuring the relationship between the properties of light emitted by the device and light received by the device after reflection by the optical media being inspected. This relationship, known as "the inspection algorithm," may be used to detect anomalies on or in the optical media being inspected.

The optical media to be inspected is typically placed on an inspection stage which orients the media optimally for a particular inspection device. Most commonly, this entails holding the optical media near its center (e.g., using a vacuum or mechanical clamp) while it is rotated to check for anomalies. As the disc is rotated, the inspection device scans the disc along the disc radius in order to check for anomalies over the entire disc surface.

Under ideal conditions the surface of the optical media being inspected is substantially flat. Under these conditions, the light reflected by the optical media follows the same path as the incident light (i.e., the light emitted by the inspection device) back to the inspection device. By comparing the light emitted to the light reflected, the inspection device can detect the presence of defects on or in the optical media. When light emitted by the inspection device reflects off an anomaly on or in the optical media, the optical characteristics of the anomaly change the properties of the reflected light received by the inspection device. The inspection device, using the inspection algorithm, registers the change in the properties of the light received after reflection and uses this information to detect and locate anomalies in or on the optical media.

However, when the optical media exhibits gross deformations such as bending or warping due to, for example, heat, humidity, improper handling or other factors, an erroneous inspection result may occur. The erroneous result may occur because the deformed surface of the optical media causes the reflected light to not follow the same path as the light emitted by the inspection device. This may cause the inspection device to improperly record the deformation as a defect, may lead to the detection of insignificant defects, i.e., defects with reflective properties that would not meet defect threshold requirements in the absence of the deformation, or may obscure defects.

In view of the foregoing, it would be desirable to provide a system and a method for accurately detecting defects on or in the optical media.

It would also be desirable to provide a system and a method for reducing erroneous optical media inspection results induced by the presence of gross deformations in the optical media.

SUMMARY OF THE INVENTION

It is an object of this invention to provide a system and a method for accurately detecting defects on or in optical media.

It is another object of this invention to provide a system and a method for reducing erroneous optical media inspection results induced by the presence of gross deformations in the optical media.

These and other objects of the invention are accomplished in accordance with the principles of the invention by providing a system and a method that allows an optical media inspection device to detect defects on or in optical media despite the presence of gross deformations (e.g., warping or bending) in the optical media that would otherwise interfere with the detection of the defects being sought.

In accordance with the present invention, the optical media to be inspected is placed on an inspection stage which orients the media optimally for a particular inspection device. This entails holding the optical media near its center while it is rotated to check for anomalies. The holding device used to hold the optical media near the center while it is rotated could be a mechanical clamp, vacuum, or any similar device which is capable of releasably holding the optical media.

Beneath the optical media is a negative displacement prohibitor which prevents negative displacement of the optical media, i.e., downward displacement in the vertical direction. The negative displacement prohibitor may be any substantially hard surface, such as a metal or plastic block. The negative displacement prohibitor may be spaced apart along the circumference of the optical media being inspected to prevent negative displacement of the optical media without inhibiting rotation of the optical media.

A conventional inspection device such as a CCD camera, laser diode, or any similar inspection device may be used to inspect the optical media for anomalies. The inspection device detects anomalies by measuring the relationship between the properties of light emitted by the device and light received by the device after reflection by the optical media being inspected. The inspection device may be connected to a screen display to provide a visual representation in graphical form of the relationship between the light emitted by the inspection device and the light reflected back to the inspection device. This graphical representation, known as a "grey scale waveform," exhibits excursions indicative of defects in or on the optical media being inspected.

In accordance with the present invention, positive displacement of the optical media under inspection (i.e., upward displacement in the vertical direction) is prevented by a positive displacement inhibitor. The positive displacement inhibitor is provided by air pressure exerted on the optical media. The pressure exerted firmly presses the optical media, keeping it substantially flat without inhibiting rotation of the optical media. Efficient positive displacement is achieved when the air pressure contacts the optical media at an angle. Preferably, the air pressure contacts the optical media at an angle of 45 degrees.

The pressure exerted on the optical media may either be controlled manually by an operator viewing the grey scale waveform, or may be controlled by a closed-loop feedback system connected to the inspection device. The closed-loop feedback system varies air pressure exerted on the optical media in response to information from the inspection device.

BRIEF DESCRIPTION OF THE DRAWINGS

The above and other objects and advantages of the present invention will be apparent upon consideration of the following detailed description, taken in conjunction with the accompanying drawings, in which like reference characters refer to like parts throughout, and in which.

DETAILED DESCRIPTION OF THE PREFERRED EMBODIMENTS

For purposes of illustration, the invention will be described for the most part in the context of its application to digital versatile discs ("DVDs"). It will be understood, however, that the invention is equally applicable to other types of optical media including but not limited to CDs, CD ROMs, and the like.

Figure 1:
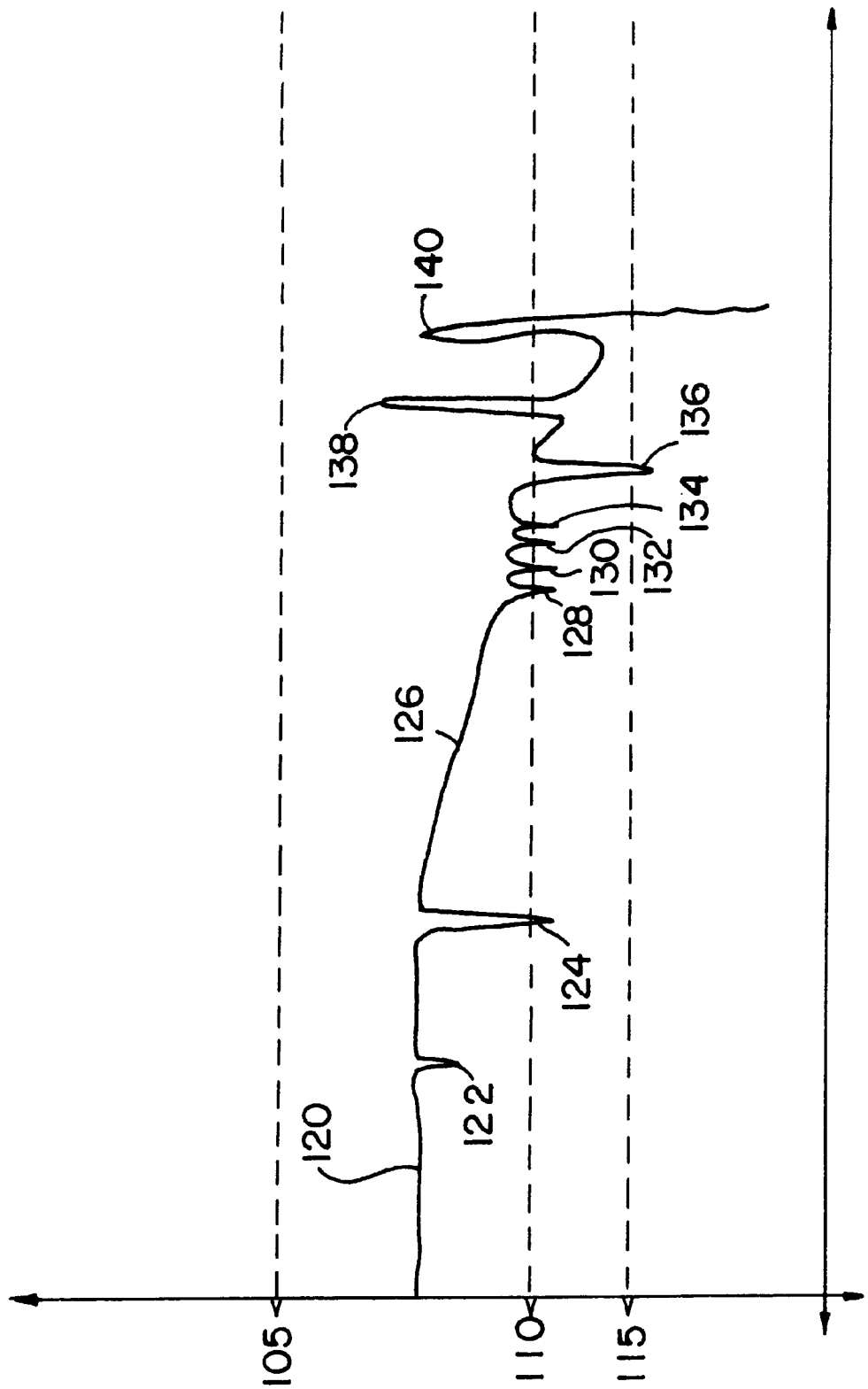
FIG. 1 is an illustrative screen display depicting a grey scale waveform representing the results of the inspection of an optical disc having a deformation that may interfere with defect inspection of the disc.

FIG. 1 is an illustrative screen display of a grey scale waveform 120 from a DVD that exhibits a gross deformation (e.g., warping or bending) that may interfere with the inspection of the optical media. The grey scale waveform 120 graphically represents the relationship between the properties of light emitted by an inspection device (described below in connection with FIGS. 3 and 5) and light received by the inspection device after the light is reflected by the DVD being inspected for defects. When the DVD being inspected is substantially flat (i.e., does not exhibit gross deformations) and has no anomalies on its surface or in one or more of the layers forming the DVD, the amount of light reflected back to the inspection device is substantially constant. When plotted as a grey scale waveform on a screen display as shown in FIG. 1, with the amount of light received after reflection represented along the y-axis and the radius of the DVD being inspected along the x-axis, the reading, being constant, is substantially parallel to the x-axis.

When an anomaly is detected on the DVD by the inspection device, the grey scale waveform exhibits an excursion 122 having a substantial drop and/or an excursion 138 having a substantial rise relative to the earlier relatively constant waveform. The appearance of these excursions on the grey scale waveform may be used to detect and locate defects on or in the DVD, i.e., physical deformities, contamination, etc. In particular, if an excursion exhibits a rise or fall having a magnitude that exceeds a prescribed threshold, then the inspection system may register a defect on the DVD at a location that corresponds to the appearance of the excursion in the grey scale waveform.

User defined thresholds 105, 110 and 115 establish different criteria for tolerance of defects on or in the optical media that may cause the light received by the inspection device after reflection off the defects on the DVD to be above or below a user established base line. Each user defined threshold may correspond to a respective acceptable tolerance of the inspection system. The inspection system may be defined to accept an excursion that crosses threshold 110, but does not cross threshold 115 (as represented by excursion 124), provided this excursion does not occur within a certain distance of other excursions. For example, the inspection system may be defined to accept a defect which results in an excursion in the waveform that crosses the threshold 110 and does not exceed the threshold 115, provided no more than three similar excursions occur within a 10 mm distance of the DVD being inspected. Similarly, the inspection system may be defined such that any excursion that crosses the threshold 115 would be registered as a defect.

The DVD being inspected is likely to be more reflective in the lead-in area that rings the innermost data area and the lead-out area that rings the outermost data area. This may result in the appearance of an excursion in the grey scale waveform that is significantly greater than the magnitude of the portion of the grey scale associated with inspection of the data area. Threshold 105 is indicative of the acceptable change in the grey scale waveform due to reflection off the areas of the DVD along the inner and outer circumference which have no data on it and are more reflective. Thus, the inspection system registers as defects any excursions that cross the threshold 105, but ignores all other excursions that fall between thresholds 105 and 110.

However, the prescribed thresholds 105, 110 and 115 can only effectively aid in the detection of defects on or in the DVD with a desired degree of accuracy if the grey scale waveform 120 stays substantially parallel to the x-axis in the absence of defects. If the surface of the DVD being inspected is not substantially flat, due to thermal or other factors, an erroneous inspection result may occur. This erroneous result is due to changes in the inspection algorithm caused by a change in the angles of incidence and reflection relative to the surface of the DVD. The erroneous result causes the grey scale waveform 120 to exhibit an undesirable gradual rise or drop corresponding to the deformations in the DVD. This gradual rise or drop may cause the inspection system to erroneously report defects that do not exist, may lead to the detection of insignificant defects, i.e., defects with reflective properties that would not meet defect threshold requirements in the absence of the deformation, or may obscure defects.

The effect of a deformation of the DVD being inspected is shown by segment 126 of waveform 120. Segment 126 is caused by the surface of the DVD not being substantially flat, as is evident from its gradual drop from an earlier substantially constant value. Due to a gradual drop from an earlier substantially constant value, excursions 128, 130, 132, 134 and 136 in the grey scale waveform are incorrectly registered by the inspection system to be defects because excursions 128, 130, 132 and 134 (more than three excursions) cross the threshold 110 within a 10 mm distance of the DVD being inspected, and excursion 136 crosses threshold 115. Moreover, excursion 138 that should have exceeded the threshold 105 and would have been registered as a defect is obscured due to a gradual drop in the waveform.

Figure 2:
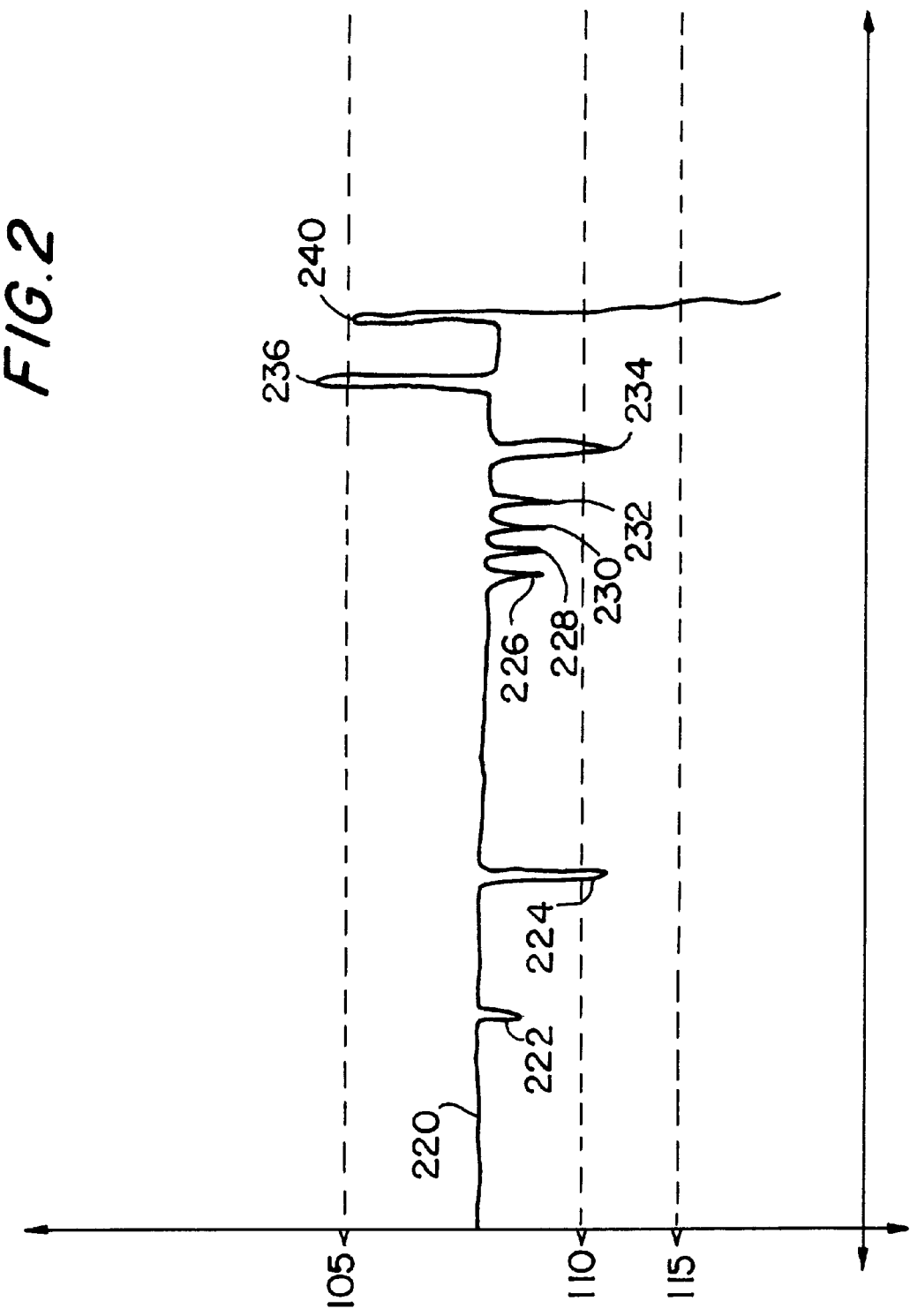
FIG. 2 is an illustrative screen display depicting a grey scale waveform representing the results of the inspection of an optical disc having a deformation that has been corrected for purposes of disc inspection in accordance with the present invention.

FIG. 2 is an illustrative screen display of a grey scale waveform 220 from an inspection device inspecting a DVD in accordance with the principles of the present invention. As is evident from the appearance of the grey scale waveform 220, the use of the present invention during DVD inspection keeps the DVD substantially flat thereby causing the grey scale waveform 220 to be substantially parallel to the x-axis until the appearance of excursion 222. Keeping the DVD substantially flat prevents excursions 226, 228, 230, 232 and 234 from being incorrectly registered as defects. At the same time, excursion 236 is registered as a defect and is not obscured due to a gradual drop in the waveform. The excursion 240, similar to the excursion 140 (FIG. 1) is due to reflection off the lead-out area that rings the outermost data area and has relatively better reflective characteristics than the area with data.

It should be understood from the aforementioned discussion that if the grey scale waveform is not substantially parallel to the x-axis until an anomaly is detected, an excursion which should not register as a defect may be registered as one because the corresponding change in the grey scale waveform may exceed the prescribed thresholds 110 and/or 115. Alternatively, an excursion which should have registered as a defect may go unnoticed if the grey scale waveform is not substantially parallel to the x-axis until an anomaly is detected.

Figure 3:
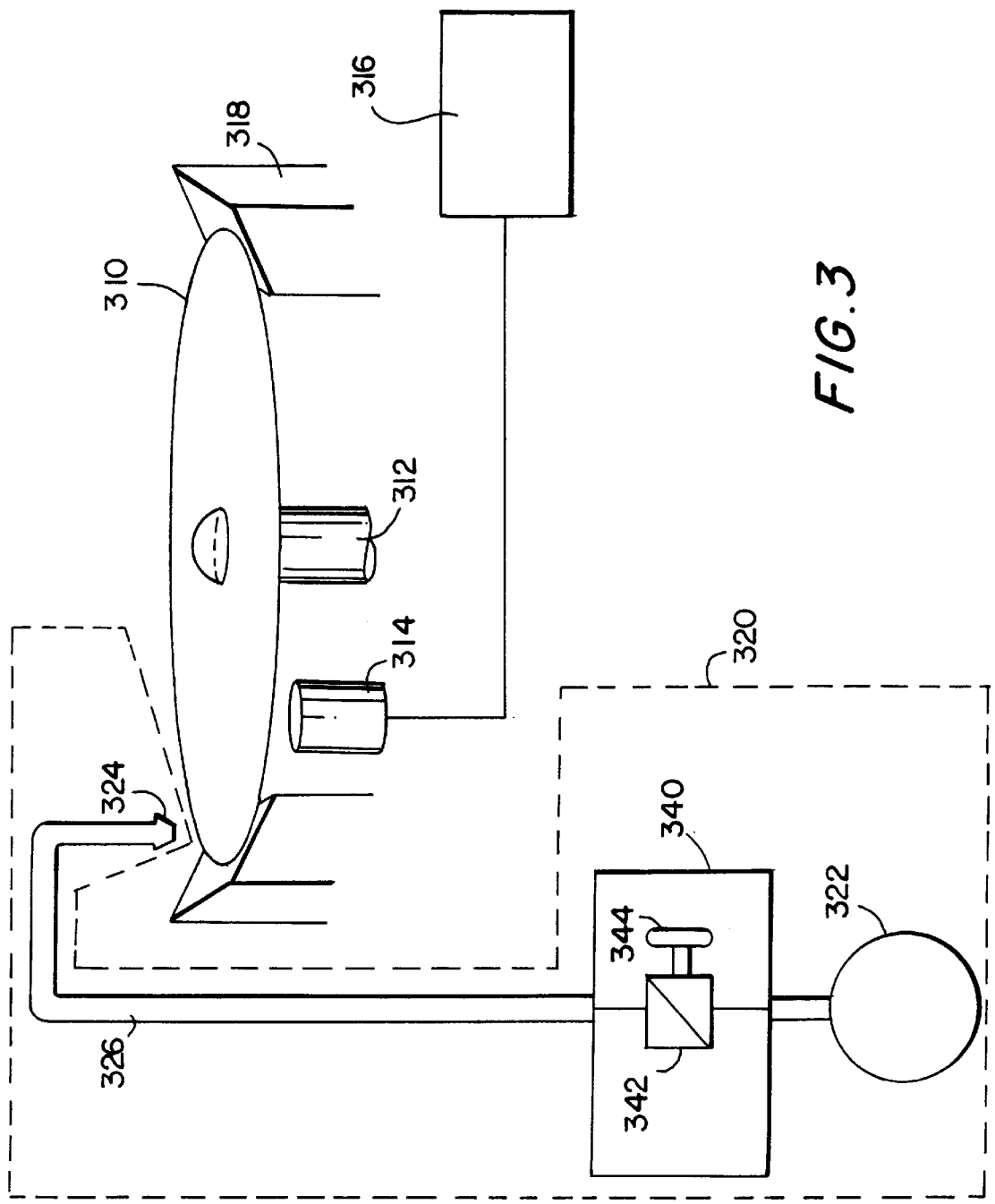
FIG. 3 is a partial elevational view of an illustrative embodiment of a system for inspecting optical media in accordance with the present invention.

In the illustrative embodiment of the present invention shown in FIG. 3, a DVD 310 is held near its center by a holding device 312. The holding device 312 may be a vacuum that releasably holds the DVD 310 while it is being rotated about its center axis for inspection. The vacuum may be generated using any of various methods commonly known in the industry. Though the illustrative embodiment of the invention shown in FIG. 3 uses a vacuum to hold the DVD 310, it will be understood that the holding device could also be a mechanical clamp or any other similar device capable of releasably gripping the DVD 310 while it is being rotated.

A conventional inspection device 314 inspects the surface of the DVD 310 for anomalies by measuring the relationship between the property of light emitted and light received after reflection against the surface of the DVD 310. The inspection device 314 may be a CCD camera, laser diode, or other similar inspection device. As described earlier, this relationship, known as the inspection algorithm, may be represented as a grey scale waveform indicative of the amount of light received by the inspection device after reflection along the y-axis, and the disc radius along the x-axis on a screen display 316. The graphical representation of the relationship between the properties of light emitted by the inspection device and the light received by the inspection device after the light is reflected by the DVD being inspected for defects, i.e., the grey scale waveform, may be generated on a screen display 316 using a processor (not shown) integrated with the inspection device 314. Alternatively, a processor incorporated into the screen display 316 may be used to generate the graphical representation. When an anomaly is detected by the inspection device 314, depending upon its reflective characteristics, it appears on the grey scale waveform as an excursion that sharply drops and/or rises.

Beneath the DVD 310 are negative displacement prohibitors 318 that impede negative displacement of the DVD 310, i.e., downward displacement in the vertical direction. The negative displacement prohibitors 318 have a substantially hard surface and can be moved horizontally, toward or away from each other, to optimally accommodate optical media of varying sizes. Horizontal displacement can be achieved manually or by a mechanically, hydraulically, or pneumatically controlled device (not shown).

A positive displacement inhibitor 320 impedes positive displacement of the DVD 310, i.e., upward displacement in the vertical direction. This is accomplished using an air pump 322 that supplies air to an air-nozzle 324 via a tube 326. Air pressure from the air-nozzle 324 directed toward the surface of the DVD 310 presses the DVD 310 downward against the negative displacement prohibitor 318 to hold it substantially flat. Efficient positive displacement is achieved when the air pressure contacts the optical media at an angle. Preferably, the air pressure contacts the optical media at an angle of 45 degrees.

In the illustrative embodiment shown in FIG. 3, air pressure at the air-nozzle 324 is controlled manually by an operator using a controller 340. The operator monitors the screen display 316 for a grey scale waveform indicative of a gross deformation, as shown in FIG. 1. In the event of such an observation, the operator may choose to increase or decrease air pressure at the air-nozzle 324 by regulating a control valve 342 via the control knob 344. The controller 340 is preferably a conventional switching mechanism that is capable of gradually varying the state of the control valve 342 between a fully closed to a fully open position. As the operator adjusts the air pressure using the controller 340, the operator monitors the screen display 316 to determine when sufficient air pressure is being supplied by the air nozzle 324 to flatten out the deformation in the DVD 310 which may interfere with defect detection by the inspection device 314.

Figure 4:
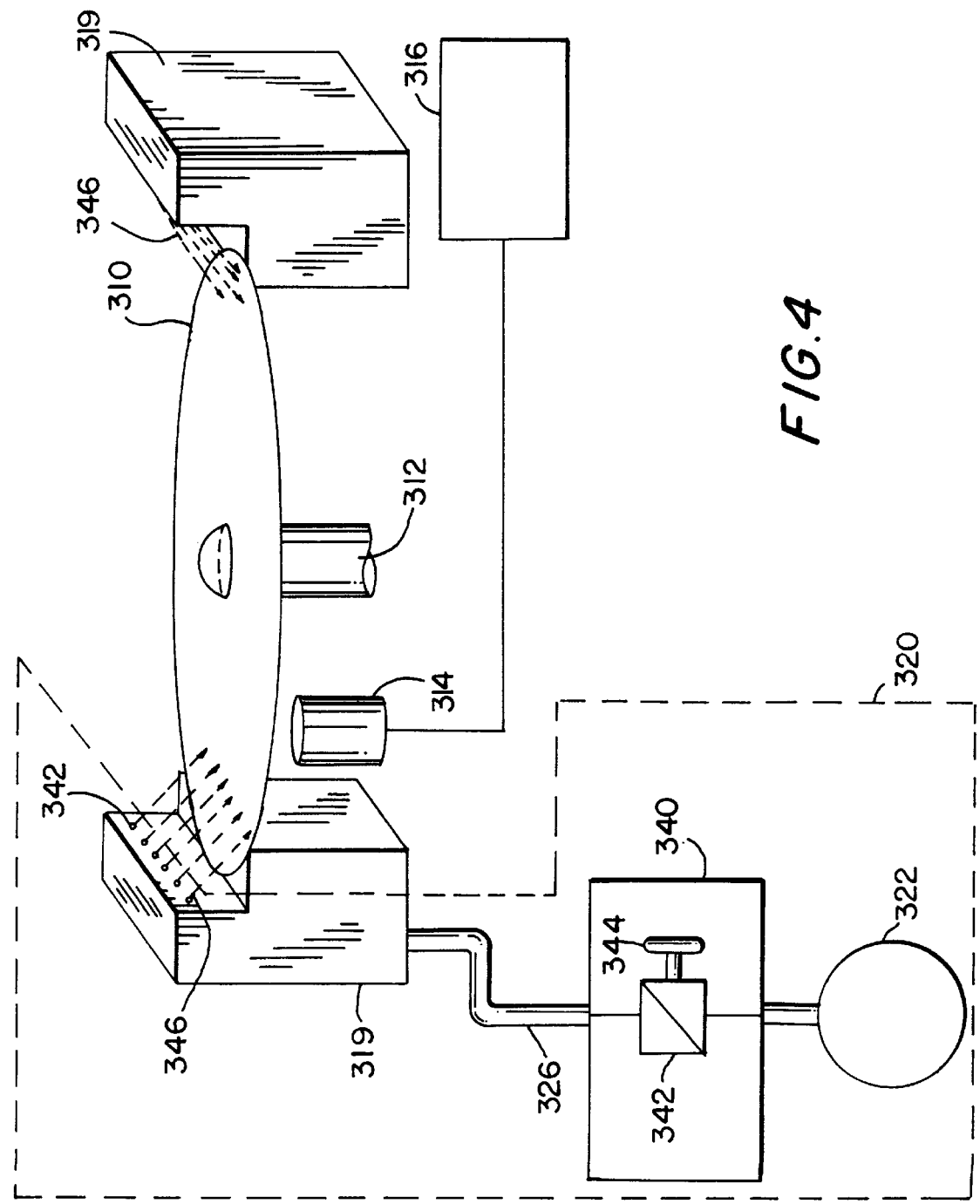
FIG. 4 is a partial elevational view of another illustrative embodiment of a system for inspecting optical media in accordance with the present invention.

In the illustrative embodiment shown in FIG. 4, aside from prohibiting the DVD 310 being inspected from the downward displacement, the negative displacement prohibitors 319 have orifices 342 through which air pressure is directed toward the surface of the DVD 310 thereby pressing the DVD 310 downward against the negative displacement prohibitors 319, to hold it substantially flat. This is accomplished using an air pump 322 that supplies air to the orifices 342 via a tube 326. Tube 326 may supply air to the orifices 342 through a manifold (not shown) having an inlet coupled to the tube 326 and outlets coupled to a respective one of the orifices 342. The orifices 342 are angled such that air flowing through them is directed toward the surface of the DVD 310 being inspected at an angle of about 45 degrees, as shown generally by the directional arrows 346. Alternatively, the orifices may be spaced along the longitudinal axis of a tubular structure which can be rotated along its longitudinal axis to direct air pressure at any desired angle toward the surface of the DVD 310 being inspected.

Figure 5:
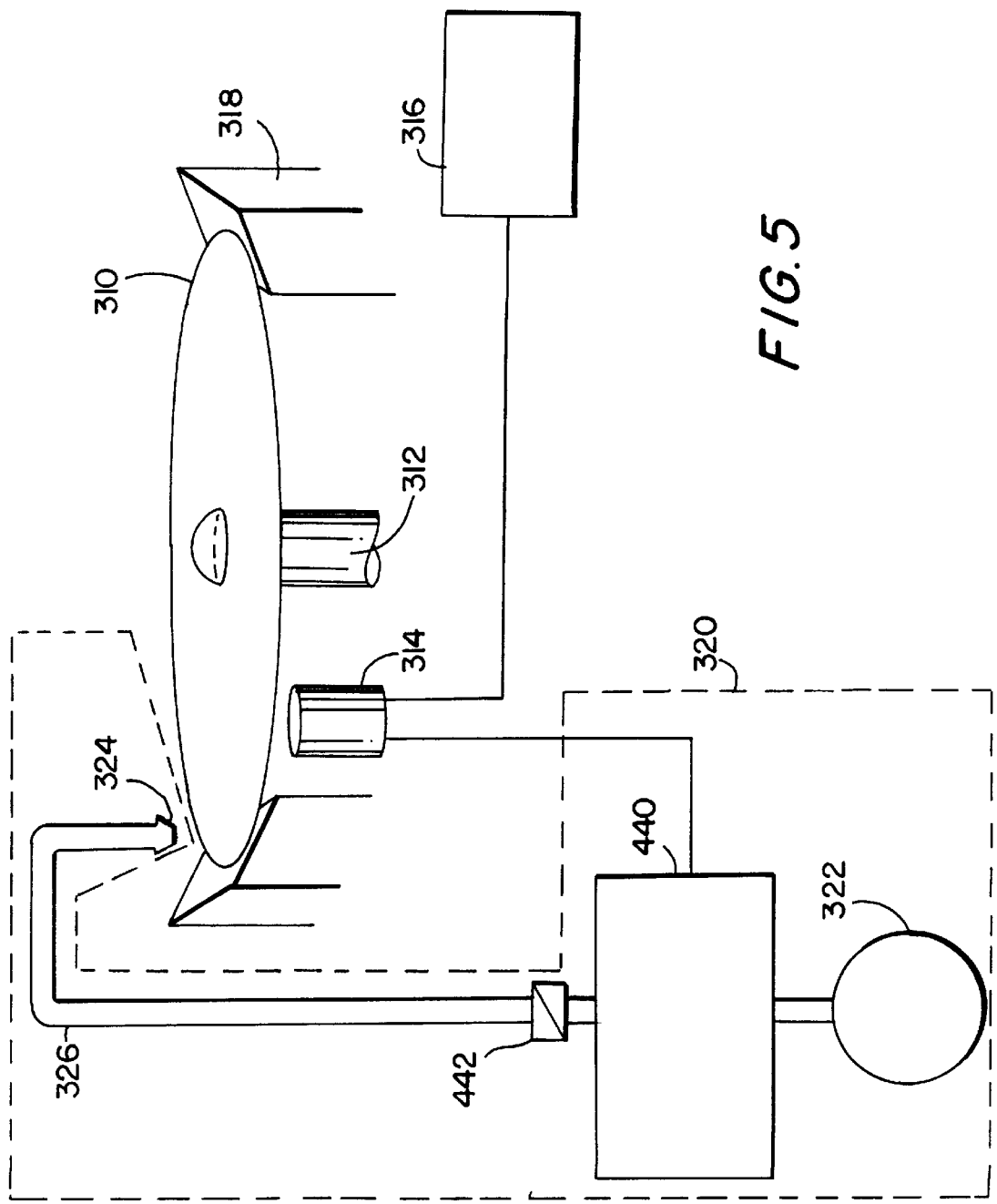
FIG. 5 is a partial elevational view of yet another illustrative embodiment system for inspecting optical media in accordance with the present invention.

In another embodiment of the present invention, shown in FIG. 5, air pressure at the air-nozzle 324 is controlled by a closed-loop feedback system 440, which is also connected to the inspection device 314. The closed-loop feedback system 440 varies air pressure at the air nozzle 324 in response to information from the inspection device 314 by controlling a control valve 442. The closed-loop feedback system 440 may use information provided by the inspection device 314 to determine automatically the extent to which the closed-loop feedback system opens or closes the control valve 442.

The closed-loop feedback system 440 may utilize information received from the inspection device 314 to generate an error signal. The closed-loop feedback system 440 may take into consideration the excursions, i.e., sharp rise or drop, in the grey scale waveform, the number of excursions and the distance over which they occur, and changes in the readings of the grey scale waveform. This information is used in determining if the excursions in the grey scale waveform are due to an anomaly of the type being sought, or if the change in the grey scale waveform reading is a result of the DVD 310 not being substantially flat. Excursions with a sharp rise or drop outside the prescribed thresholds 105 or 115, as well as multiple excursions within a specified distance that exceed the prescribed threshold 110 (as shown in FIGS. 1 and 2) are indicative of an anomaly of the type being sought. However, gradual changes in the grey scale waveform readings, as well as gradual changes in the grey scale waveform readings over a relatively long period of time are a result of the DVD 310 not being substantially flat (as shown in FIG. 1). Excursions that do not exceed the prescribed thresholds are ignored as not being indicative of the defects being sought.

Only in the event the closed-loop feedback system 440 confirms that the change in the grey scale waveform readings is due to the DVD 310 not being substantially flat is an error signal generated which causes the control valve 442 to vary the pressure of air coming out of the air-nozzle 324 such that the error signal is reduced. The closed-loop feedback system 440 receives information from the inspection device 314 on an ongoing basis during DVD testing to regulate air pressure at the air-nozzle 324 by regulating the control valve 442. However, for optimal results air pressure at air-nozzle 324 should be adjusted between the values of about 0 and 6 bars.

Figure 6:
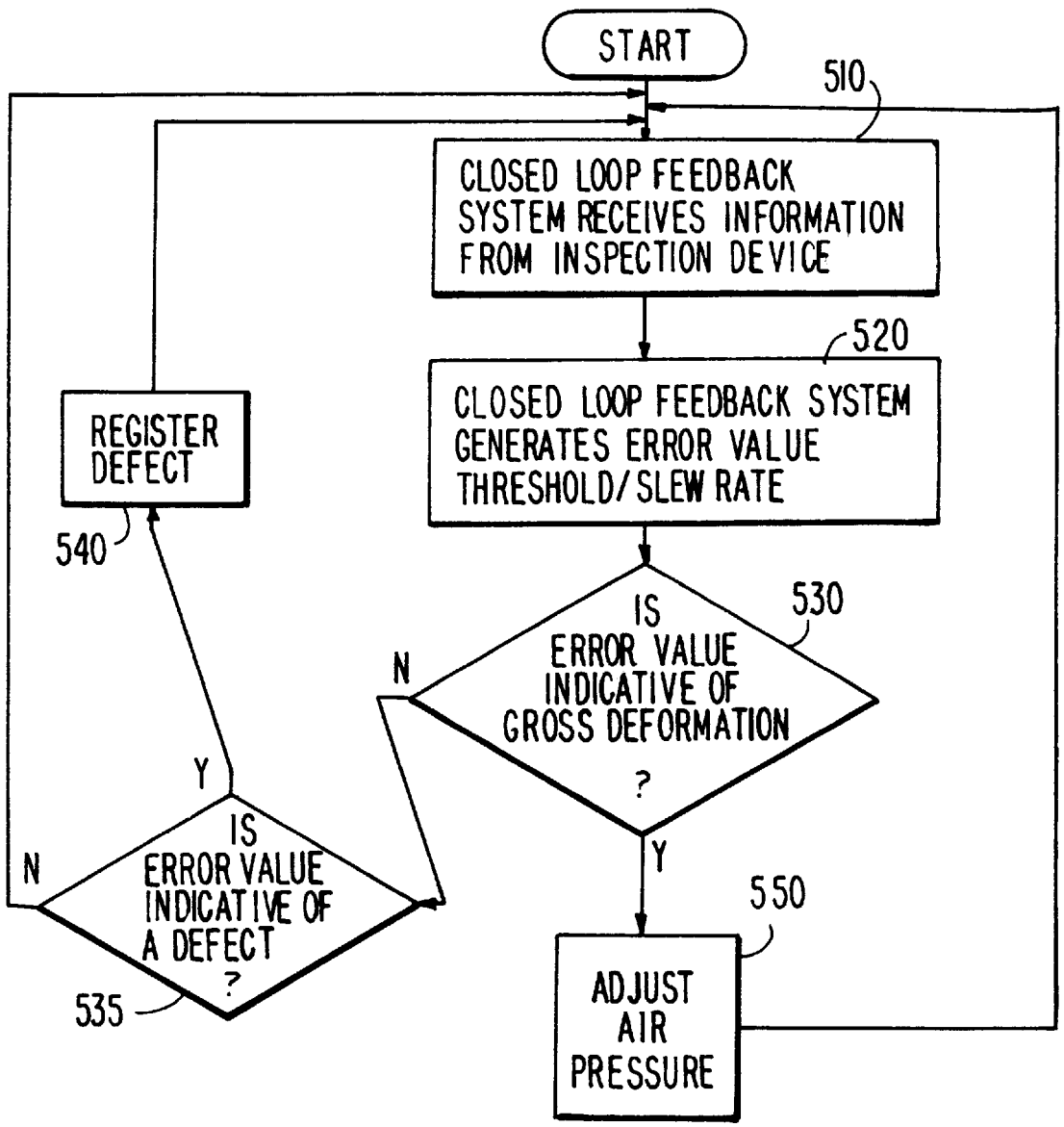
FIG. 6 is a logic flow diagram representing a sequence of steps performed by the closed-loop feedback system shown in FIG. 5.

FIG. 6 shows a logic flow diagram representing the sequence of steps required for maintaining the DVD substantially flat using the closed-loop feedback system 440 (FIG. 5). The sequence starts by the closed-loop feedback system 440 (FIG. 5) receiving information from the inspection device 314 (FIG. 5) at step 510. At step 520, the closed-loop feedback system 440 (FIG. 5) uses the information received at step 510 to generate an error value by comparing the information received to the defined thresholds and/or the number of occurrences of excursions that exceeds an established threshold value over a established distance over which the DVD has been inspected, as well as the change in readings of the grey scale waveform. At step 530, closed-loop feedback system 440 (FIG. 5) determines whether the error value generated at step 520 is indicative of a defect on or in the DVD, or is indicative of a gross deformation of the DVD (e.g., bending or warping). The closed-loop feedback system 440 (FIG. 5) may do this by comparing the error value generated at step 520 to a range of acceptable values as well as by determining the slew rate.

If, at step 530, it is determined that the error value generated at step 520 is indicative of a defect, then, at step 535, closed-loop feedback system 440 (FIG. 5) determines whether the error value generated at step 520 corresponds to a defect in or on the DVD that exceeds the range established by the prescribed thresholds 105, 110 and 115 (FIGS. 1 and 2), i.e., a defect that needs to be registered, or it is a defect that falls within the prescribed thresholds 105, 110 and 115 (FIGS. 1 and 2) and need not be registered. If at step 535 it is established that the error value generated at step 520 is indicative of a defect that exceeds the range established by the prescribed thresholds 105, 110 and 115 (FIGS. 1 and 2), then, after the defect is registered at step 540, the system returns to step 510 to continue the monitoring. However, if at step 535 it is established that the error value generated at step 520 is indicative of a defect that falls within the range established by the prescribed thresholds 105, 110 and 115 (FIGS. 1 and 2), then the system returns to step 510 to continue the monitoring of the information from the inspection device without registering the defect.

However, if at step 530 the closed-loop feedback system 440 (FIG. 5) determines that the information received is indicative of a gross deformation, it generates a signal that causes the air pressure to be adjusted at step 550. The air pressure is adjusted to cause the error value to fall within an acceptable range. Thereafter, the system returns to step 510 to continue the monitoring.

As indicated before, it will be appreciated that the system of this invention is equally effective with optical media other than DVDs, for inspection for anomalies by an inspection device.

It will be understood that the foregoing is only illustrative of the principles of the invention and that various modifications can be made by those skilled in the art without departing from the scope and spirit of the invention. For example, instead of varying the air pressure by a control valve it could be varied by changing the aperture of the air-nozzle. Similarly, more than one air-nozzle can be used to achieve an equilibrium rendering the surface of the optical media to be inspected substantially flat. Moreover, the closed-loop feedback system 440 (FIG. 5) could also be used to control the air pressure at the orifices 342 (FIG. 4) in the negative displacement prohibitors 319 (FIG. 4).

Thus a system and a method are provided that allow an optical media inspection device to detect defects on or in optical media despite the presence of gross deformations (e.g., bending or warping) in the media that would otherwise interfere with the inspection process. One skilled in the art will appreciate that the present invention can be practiced by other than the described embodiments, which are presented for purposes of illustration and not of limitation, and the present invention is limited only by the claims which follow.

The invention claimed is:

1. An apparatus for facilitating inspection of optical media, comprising:
   an inspection device for inspecting said optical media;
   a holding device for releasably holding said optical media to be inspected;
   a negative displacement prohibitor for impeding displacement of said optical media in a first direction; and
   a positive displacement inhibitor for impeding displacement of said optical media in a second direction.

2. The apparatus of claim 1 wherein said negative displacement prohibitor and said positive displacement inhibitor keep said optical media substantially flat.

3. The apparatus of claim 1 wherein said holding device is a vacuum.

4. The apparatus of claim 1 wherein said negative displacement prohibitor comprises two blocks spaced apart along said optical media's circumference, said blocks having a substantially hard surface.

5. The apparatus of claim 1 wherein said first direction is opposite said second direction.

6. The apparatus of claim 1 further comprising a screen display for graphically representing information received from said inspection device during inspection of said optical media.

7. The apparatus of claim 1 wherein said positive displacement inhibitor comprises an air-blowing device for directing air pressure onto said optical media to flatten said optical media.

8. The apparatus of claim 7 wherein said air-blowing device comprises of orifices in said negative displacement prohibitor.

9. The apparatus of claim 1 wherein said positive displacement inhibitor comprises a controller for varying air pressure provided by an air-blowing device.

10. The apparatus of claim 9 wherein said controller comprises a closed-loop feedback system.

11. The apparatus of claim 10 wherein said closed-loop feedback system receives information from said inspection device.

12. The apparatus of claim 11 wherein said closed-loop feedback system determines the amount of air pressure to be supplied by said air blowing device using said information from said inspection device.

13. The apparatus of claim 12 wherein said information provided by said inspection device is characterized by a slew rate and said closed-loop feedback system determines the amount of said air pressure using said slew rate.

14. The apparatus of claim 10 wherein said closed-loop feedback system varies the amount of said air pressure by regulating a control valve.

15. A method of facilitating inspection of optical media by an inspection device, said method comprising the steps of:

releasably holding said optical media to be inspected by said inspection device;

impeding displacement of said optical media in a first direction; and impeding displacement of said optical media in a second direction.

16. The method of claim 15 wherein said releasably holding step comprises releasably holding said optical media near its center by a vacuum while it is rotated.

17. The method of claim 15 wherein said step of impeding displacement in said first direction comprises providing two blocks having a substantially hard surface spaced apart along said optical media's circumference, said optical media being releasably held above said blocks.

18. The method of claim 15 wherein said first direction is opposite said second direction.

19. The method of claim 15 wherein said step of impeding displacement in said second direction comprises directing air pressure onto said optical media in said first direction using an air-blowing device to flatten said optical media.

20. The method of claim 15 wherein said step of impeding displacement in said second direction further comprises varying air pressure at an air-blowing device by a controller.

21. The method of claim 20 wherein said step of impeding displacement in said second direction further comprises determining the amount of air pressure to be supplied using information received from said inspection device.

* * * * *